United States Patent [19]

Klemm

[11] Patent Number: Plant 6,094

[45] Date of Patent: Feb. 2, 1988

[54] CARNATION NAMED KLEFICAN

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 808,104

[22] Filed: Dec. 12, 1985

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of spray carnation particularly distinguished by its medium sized blooms having a bright, clear yellow color and carried on rigid, medium broad, blue-green stems, by its fast growing habit with continuous year around blooming and its resistance to Fusarium Oxysporum.

1 Drawing Figure

BACKGROUND OF THE NEW PLANT

This new spray carnation cultivar originated at Stuttgart, West Germany, as a sport of an unpatented carnation variety named "Ministar" being grown in my greenhouses for the production of cut flowers, as well as for the propagation and sale of plants to commercial growers for spray carnation uses. This sport was discovered by me at Stuttgart, West Germany, in 1981 and was selected for propagation because of its medium sized, bright and clear yellow blooms and the likelihood of its being a worthwhile addition to the commercial field of miniature carnations. Propagation of this new plant was carried on by me and under my instructions at Stuttgart, West Germany, by means of cuttings and continued propagation in that manner through several generations demonstrated that the new plant retains the characteristics of the original discovery and also that the new plant had a very fast growing habit and a very good year around production of blooms. The successive generations of this new plant have demonstrated that all of these characteristics hold true from generation to generation and appear to be firmly fixed.

DESCRIPTION OF THE DRAWING

My new miniature carnation cultivar is illustrated by the accompanying photographic drawing, which shows the inflorescence on a stem of a fully grown plant, the view including buds and flowers in several stages of development together with a face view of a fully opened blossom and with details including a bud, two stages of bud opening, separated petals, a specimen of calyx and sepals, and a specimen of an ovary.

DESCRIPTION OF THE NEW PLANT

The following is a detailed description of my new spray carnation cultivar based upon observation of plants grown under conventional greenhouse procedures at Stuttgart, West Germany, the color designations being according to The R.H.S. Colour Chart published by The Royal Horticultural Society of London, England.

THE PLANT

Origin: Sport.

Parentage: Ministar (unpatented).

Classification:

*Botanic.*—*Dianthus caryophyllus.*

*Commercial.*—Miniature carnation.

Form: Bush.

Height: About 90 to 120 cm. at first flush.

Growth: Rapid, vigorous and upright with good strength.

Branching: Normal.

Foliage:

*Quantity.*—Moderate.

*Leaf size.*—Moderate, of lanceolate shape, acuminate apex and entire margins, the foliage being sessile.

*Texture.*—Smooth.

*Color.*—Upper side — Blue-Green. Under side — Blue-Green.

THE BUD

Size: Medium.

Diameter.—About 15 mm.

*Length.*—About 40 mm.

Form: Ovate, before parting of the sepals.

Opening rate: Moderate.

Color: When sepals first divide and petals begin to unfurl — Bright yellow.

Sepals:

Character.—The sepals stand up beneath the bloom. The sepals are connected together at the calyx and extend upwardly with generally ovate form and acute apex.

*Color.*—Inside — Grey-Green. Outside — Grey-Green.

Calyx:

*Shape.*—Cylindrical.

*Size.*—Medium, about 15 mm. in diameter and about 17 mm. long.

*Splitting.*—The calyx does not split.

*Aspect.*—Smooth.

Peduncle:

*Length.*—About 40 to 45 mm.

*Character.*—Erect and rigid.

*Color.*—Grey-Green.

THE FLOWER

Blooming habit: Continuous and year around.

Size of bloom: Medium.

*Diameter.*—About 60 to 65 mm.

*Depth.*—About 30 to 35 mm.

Borne: Singly on strong, upright pedicels.

Shape: High centered when bloom first opens and as the bloom matures.

Petalage:

*Number of petals.*—About 29.

*Arrangement.*—Imbricated.

*Shape of petals.*—Fan-shaped with deeply serrated end margin.

*Texture.*—Soft.

*Appearance.*—Shiny.

*Color.*—Outer and inside petals — RHS 2-C.

Peduncle:

*Length.*—About 40 to 45 mm.

*Color.*—Grey-Green.

*Character.*—Sturdy and upright.

Persistence: The petals hang on and dry and the bloom stays upright.

Fragrance: None.

Lasting quality:

*On plant.*—About 15 days.

*As a cut flower.*—About 12 days.

REPRODUCTIVE ORGANS

Stamens:

*Arrangement.*—General. Anthers and pollen are rarely present.

Pistils:

*Number.*—Three.

Styles:

*Length.*—About 20 to 30 mm.

Stigmas:

*Color.*—White.

This new miniature carnation variety most nearly resembles "Klemstar" (unpatented) but differs in that it is a faster growing variety with a new bright, clear yellow color and its blue-green stems, which are rigid and medium broad, provide a very good form of spray.

I claim:

1. A new and distinct miniature carnation, substantially as herein shown and described, characterized by its year around productivity of bright, clear yellow flowers carried on rigid and erect pedicels in spray formation on a sturdy and upright peduncle.

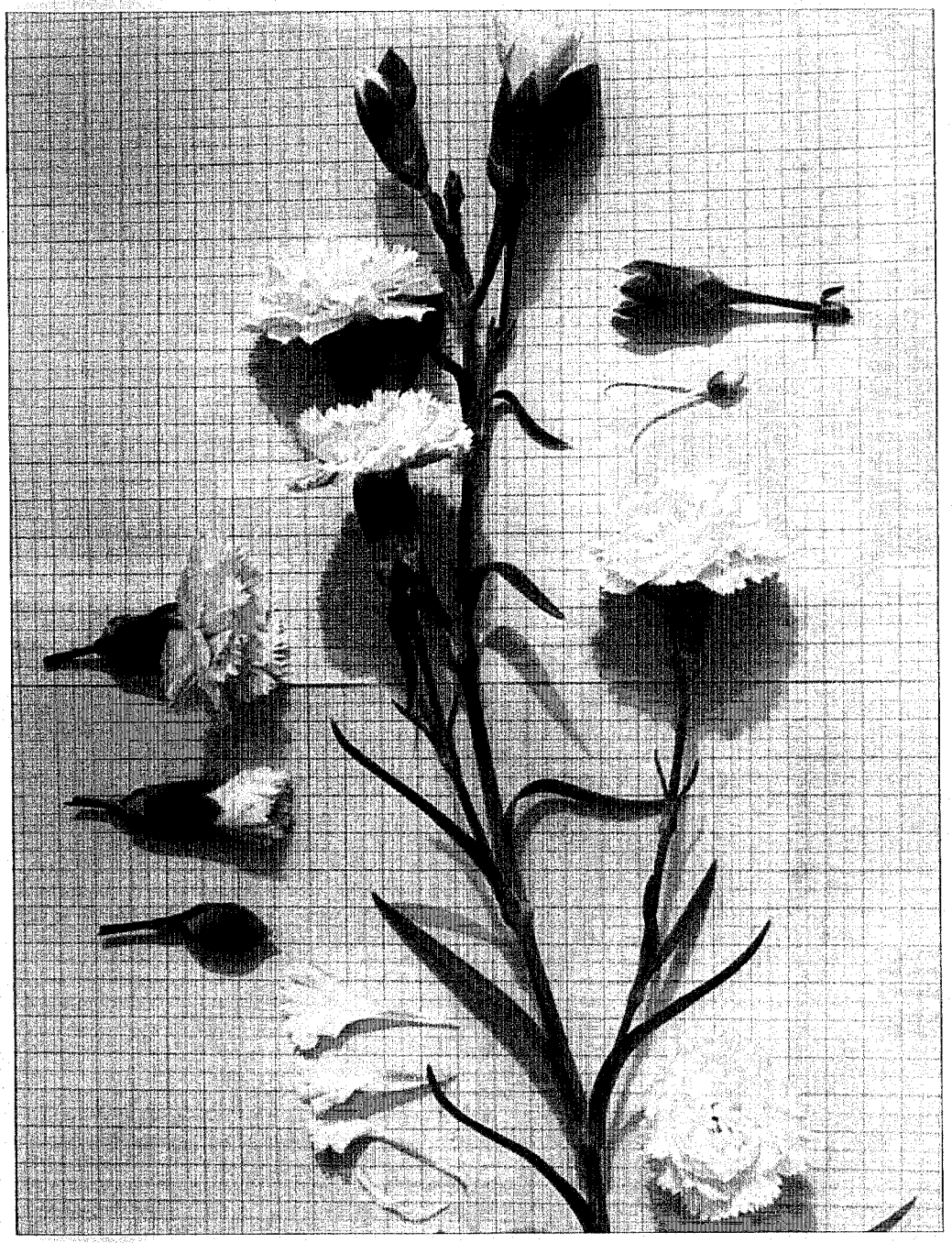

* * * * *